United States Patent
Riis et al.

(10) Patent No.: US 11,872,408 B2
(45) Date of Patent: Jan. 16, 2024

(54) NEAR INFRARED LIGHT IN HEARING AID APPLIANCES

(71) Applicant: Oticon Medical A/S, Smørum (DK)

(72) Inventors: Søren Kamaric Riis, Smørum (DK); Thomas Lunner, Smørum (DK); Dorothea Wendt, Smørum (DK); Bradford Backus, Vallauris (FR)

(73) Assignee: Oticon Medical A/S, Smørum (DK)

( * ) Notice: Subject to any disclaimer, the term of this patent is extended or adjusted under 35 U.S.C. 154(b) by 413 days.

(21) Appl. No.: 16/388,363

(22) Filed: Apr. 18, 2019

(65) Prior Publication Data

US 2019/0321655 A1 Oct. 24, 2019

(30) Foreign Application Priority Data

Apr. 19, 2018 (EP) .................................. 18168222

(51) Int. Cl.
*A61N 5/06* (2006.01)
*A61B 5/24* (2021.01)

(52) U.S. Cl.
CPC .............. *A61N 5/0622* (2013.01); *A61B 5/24* (2021.01); *A61N 5/0603* (2013.01); *A61N 2005/0605* (2013.01); *A61N 2005/0626* (2013.01); *A61N 2005/0659* (2013.01)

(58) Field of Classification Search
CPC .............. A61N 1/0541; A61N 1/36038; A61N 2005/0605; A61N 2005/0659; A61B 5/0031; A61B 5/4836; A61B 5/0059; A61B 5/0058
See application file for complete search history.

(56) References Cited

U.S. PATENT DOCUMENTS

| 8,355,793 B2 * | 1/2013 | Dadd | A61N 5/0601 |
| | | | 607/57 |
| 8,792,978 B2 * | 7/2014 | Wells | A61N 5/0603 |
| | | | 607/3 |

(Continued)

FOREIGN PATENT DOCUMENTS

| WO | WO 2018/009905 A2 | 1/2018 |
| WO | WO 2018/009905 A3 | 1/2018 |

OTHER PUBLICATIONS

Saliba et al. "Functional near-infrared spectroscopy for neuroimaging in cochlear implant recipients," Hearing Research 338 (2016) pp. 64-75.

*Primary Examiner* — Deborah L Malamud
(74) *Attorney, Agent, or Firm* — Birch, Stewart, Kolasch & Birch, LLP

(57) ABSTRACT

A cochlear implant hearing aid system is disclosed. The cochlear implant hearing aid system comprises an external part. The external part includes a sound pickup unit configured to pick up sound from the environment and a sound processing unit configured to process said sound. The cochlear implant hearing aid system further comprises an implant part. The implant part includes an implant processing unit and a plurality of cochlea stimulation electrodes for stimulation of a cochlea of a user. The cochlear implant hearing aid system further comprises a near-infrared transmitter configured to transmit a near-infrared wave. The cochlear implant hearing aid system further comprises a near-infrared receiver configured to receive said near-infrared wave.

13 Claims, 9 Drawing Sheets

(56) References Cited

U.S. PATENT DOCUMENTS

| | | | |
|---|---|---|---|
| 8,845,705 B2* | 9/2014 | Perkins | A61N 5/0622 600/25 |
| 2011/0245714 A1* | 10/2011 | Volckaerts | A61N 1/36039 607/57 |

* cited by examiner

NEAR INFRARED LIGHT IN HEARING AID APPLIANCES

TECHNICAL FIELD

The present disclosure relates to the utilization of near infrared light in hearing aid appliances.

BACKGROUND

In the field of hearing aid devices and further in particular medical fields, easy acquisition of brain activity is desirable.

For brain computer interfaces, wearable Electroencephalography (EEG) solutions have started emerging commercially and in research (e.g. EarEEG).

EEG is based on measuring very small electrical potentials resulting from communication between neurons in the brain. To measure these evoked potentials, the EEG system needs to be very sensitive.

For cochlear implant (CI) patients, electrical artifacts emitted by CI electrode(s) during stimulation is several magnitudes above the sensitivity of the EEG amplifier, and recording continuous EEG on a CI patient is very difficult and requires substantial data post-processing. Typical commercial EEG systems are not able to cope with CI artifacts (the amplifier needs time to settle after a peak artifact etc.). Typically, only single event recordings are possible (CI fires at T=0 and EEG system starts recording some milliseconds later).

Cochlear implantation in young children has been an extraordinary success, however there are individual patients that do poorly. Possible causes of poor performances are several and diverse, including less-than-optimal programming of the cochlear implant and compromised cochlear innervation. An objective test of how well speech information is received by the brain would be a helpful tool in CI research. For instance, it could provide a quantitative feedback measure in pediatric CI users who are unable to deliver an interpretable behavioral response. In older populations, it could allow an assessment between cortical and behavioral responses to speech, and potentially estimate the pattern of cochlear innervation.

Functional magnetic resonance imaging (fMRI) studies have shown that the receptive language region of the auditory cortex (the superior temporal gyrus) demonstrates more activation in response to clear speech than to scrambled speech or environmental sounds in normal-hearing subjects. However, fMRI is difficult to use in children hearing through a cochlear implant because the device is ferromagnetic and because children typically require general anesthesia to remain still during the test.

Further, in the field of hearing aid devices, a problem resides in how to transfer both data and power across the skin in a way that simultaneously optimizes the data rates and power efficiency and allows full-duplex and asynchronous forward and reverse data transfers. For example, such requirements are to be fulfilled in a cochlear implant system which requires both data and power transfer to the implant (internal implant unit) and returned data transfer back (e.g. between an external unit and the internal implant unit of the cochlear implant system).

Therefore, there is a need to provide a solution that addresses at least some of the above-mentioned problems. The present disclosure provides at least an alternative to the prior art.

SUMMARY

According to an aspect of the present disclosure, there is provided a cochlear implant hearing aid system. The cochlear implant hearing aid system comprises an external part. The external part includes a sound pickup unit configured to pick up sound from the environment and a sound processing unit configured to process said sound. The cochlear implant hearing aid system further comprises an implant part. The implant part includes an implant processing unit and a plurality of cochlea stimulation electrodes for stimulation of a cochlea of a user. The cochlear implant hearing aid system further comprises a near-infrared transmitter configured to transmit a near-infrared wave. The cochlear implant hearing aid system further comprises a near-infrared receiver configured to receive said near-infrared wave.

The near-infrared transmitter may be an internal near-infrared transmitter provided on said implant part and configured to transmit said near-infrared wave towards a cortex of said user. In such case, the near-infrared receiver may be an internal near-infrared receiver provided on said implant part and configured to receive said near-infrared wave scattered by said cortex of said user.

The cochlear implant hearing aid system may further comprise an external near-infrared transmitter configured to transmit said near-infrared wave towards said internal near-infrared receiver. In such case, the internal near-infrared receiver may be further configured to receive said near-infrared wave directly from said external near-infrared transmitter.

The near-infrared transmitter may be an external near-infrared transmitter provided on said external part. In such case, the near-infrared receiver may be an internal near-infrared receiver provided on said implant part.

The external near-infrared transmitter may be configured to transmit said near-infrared wave towards a cortex of said user. In such case, the internal near-infrared receiver may be configured to receive said near-infrared wave scattered by said cortex of said user.

The external near-infrared transmitter may be configured to transmit said near-infrared wave towards said internal near-infrared receiver. In such case, the internal near-infrared receiver may be configured to receive said near-infrared wave directly from said external near-infrared transmitter.

The near-infrared transmitter may be an internal near-infrared transmitter. In such case, the near-infrared receiver may be an external near-infrared receiver. Further, in such case, the internal near-infrared transmitter may be configured to transmit said near-infrared wave towards said external near-infrared receiver. Further, in such case, the external near-infrared receiver may be configured to receive said near-infrared wave directly from said internal near-infrared transmitter.

In the above cases, "directly" preferably means "in a straight line potentially through tissue". While diffracted light is included, a change in the direction e.g. through reflection is preferably excluded.

The implant processing unit may be configured to process said near-infrared wave scattered by said cortex of said user to determine a brain activity of a brain of said user.

The near-infrared wave scattered by said cortex may be indicative of hemodynamic responses associated with neuron behavior of said brain of said user.

A result of said implant processing unit may be used for adapting a signal processing of said cochlear implant hearing aid system. Alternatively, or in addition, a result of said implant processing unit may be used for adapting a processing of said sound by said sound processing unit. Alternatively, or in addition, a result of said implant processing unit may be used for fitting said cochlear implant hearing aid system to said user. Alternatively, or in addition, a result of said implant processing unit may be used for health condition monitoring of said user. Alternatively, or in addition, a result of said implant processing unit may be used for an output of a brain-computer-interface.

The near-infrared wave transmitted by said external near-infrared transmitter towards said internal near-infrared receiver may comprise encoded data to be used for said stimulation of said cochlea of said user by said cochlea stimulation electrodes.

The cochlear implant hearing aid system may further comprise an electromagnetic power transmission unit provided on said external part and configured to transmit electromagnetic power in a non-contact manner. In such case, the cochlear implant hearing aid system may further comprise an electromagnetic power receiving unit provided on said implant part and configured to receive said electromagnetic power in a non-contact manner. Further, in such case, the implant part may be configured to utilize said electromagnetic power as a power supply.

The cochlear implant hearing aid system may further comprise an electromagnetic data transmission unit provided on said implant part and configured to transmit data in a non-contact manner utilizing an electromagnetic field generated by said electromagnetic power transmission unit for transmission of said electromagnetic power. In such case, the cochlear implant hearing aid system may further comprise an electromagnetic data receiving unit provided on said external part and configured to receive said data in a non-contact manner.

The cochlear implant hearing aid system may further comprise a power adjustment unit provided on said external part and configured to adjust, based on said data, said electromagnetic power transmitted by said electromagnetic power transmission unit.

The cochlear implant hearing aid system may further comprise a wave transmission adjustment unit provided on said external part and configured to adjust, based on said data, said near-infrared wave transmitted by said external near-infrared transmitter towards said internal near-infrared receiver.

The near-infrared wave may be a wave having a wavelength equal to or larger than 700 nm and equal to or smaller than 900 nm.

Here, "equal to or larger than 700 nm and equal to or smaller than 900 nm" means that the wavelength is a wavelength between and including 700 nm and 900 nm. In other words, in such case the wavelength is a wavelength out of a range defined by (and including) 700 nm and 900 nm.

BRIEF DESCRIPTION OF DRAWINGS

The aspects of the disclosure may be best understood from the following detailed description taken in conjunction with the accompanying figures. The figures are schematic and simplified for clarity, and they just show details to improve the understanding of the claims, while other details are left out. Throughout, the same reference numerals are used for identical or corresponding parts. The individual features of each aspect may each be combined with any or all features of the other aspects. These and other aspects, features and/or technical effect will be apparent from and elucidated with reference to the illustrations described hereinafter in which:

DETAILED DESCRIPTION

Figure 1:
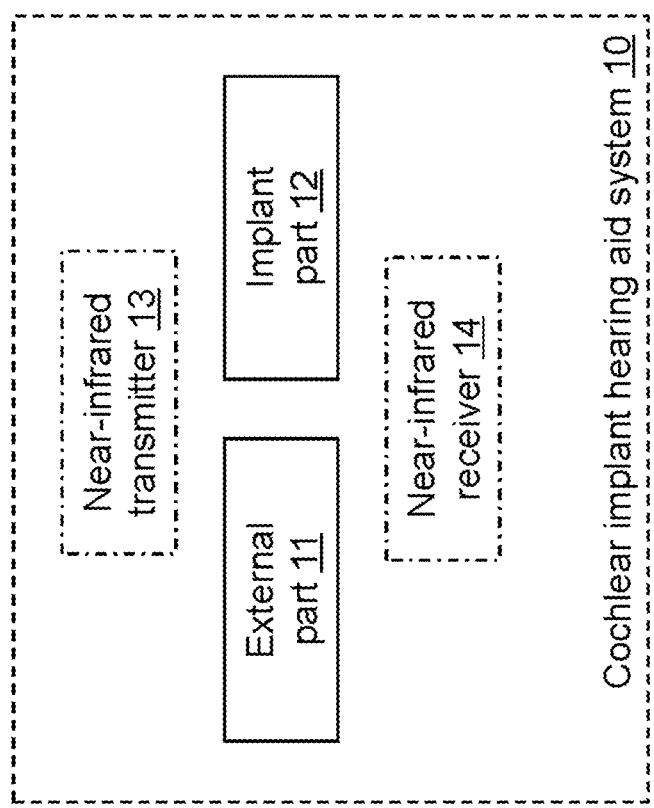
FIG. 1 illustrates a cochlear implant hearing aid system according to an embodiment of the disclosure.

The detailed description set forth below in connection with the appended drawings is intended as a description of various configurations. The detailed description includes specific details for the purpose of providing a thorough understanding of various concepts. However, it will be apparent to those skilled in the art that these concepts may be practiced without these specific details. Several aspects of the apparatus and methods are described by various blocks, functional units, modules, components, circuits, steps, processes, algorithms, etc. (collectively referred to as "elements"). Depending upon particular application, design constraints or other reasons, these elements may be implemented using electronic hardware, computer program, or any combination thereof.

The electronic hardware may include microprocessors, microcontrollers, digital signal processors (DSPs), field programmable gate arrays (FPGAs), programmable logic devices (PLDs), gated logic, discrete hardware circuits, and other suitable hardware configured to perform the various functionality described throughout this disclosure. Computer program shall be construed broadly to mean instructions, instruction sets, code, code segments, program code, programs, subprograms, software modules, applications, software applications, software packages, routines, subroutines, objects, executables, threads of execution, procedures, functions, etc., whether referred to as software, firmware, middleware, microcode, hardware description language, or otherwise.

A hearing device may include a hearing aid that is adapted to improve or augment the hearing capability of a user by receiving an acoustic signal from a user's surroundings, generating a corresponding audio signal, possibly modifying the audio signal and providing the possibly modified audio signal as an audible signal to at least one of the user's ears. The "hearing device" may further refer to a device such as an earphone or a headset adapted to receive an audio signal electronically, possibly modifying the audio signal and providing the possibly modified audio signals as an audible signal to at least one of the user's ears. Such audible signals may be provided in the form of an acoustic signal radiated into the user's outer ear, or an acoustic signal transferred as mechanical vibrations to the user's inner ears through bone structure of the user's head and/or through parts of middle ear of the user or electric signals transferred directly or indirectly to cochlear nerve and/or to auditory cortex of the user.

The hearing device is adapted to be worn in any known way. This may include i) arranging a unit of the hearing device behind the ear with a tube leading air-borne acoustic signals into the ear canal or with a receiver/loudspeaker arranged close to or in the ear canal such as in a Behind-the-Ear type hearing aid, and/or ii) arranging the hearing device entirely or partly in the pinna and/or in the ear canal of the user such as in a In-the-Ear type hearing aid or In-the-Canal/Completely-in-Canal type hearing aid, or iii) arranging a unit of the hearing device attached to a fixture implanted into the skull bone such as in Bone Anchored Hearing Aid or Cochlear Implant, or iv) arranging a unit of the hearing device as an entirely or partly implanted unit such as in Bone Anchored Hearing Aid or Cochlear Implant.

A "hearing system" refers to a system comprising one or two hearing devices, and a "binaural hearing system" refers to a system comprising two hearing devices where the devices are adapted to cooperatively provide audible signals to both of the user's ears. The hearing system or binaural hearing system may further include auxiliary device(s) that communicates with at least one hearing device, the auxiliary device affecting the operation of the hearing devices and/or benefiting from the functioning of the hearing devices. A wired or wireless communication link between the at least one hearing device and the auxiliary device is established that allows for exchanging information (e.g. control and status signals, possibly audio signals) between the at least one hearing device and the auxiliary device. Such auxiliary devices may include at least one of remote controls, remote microphones, audio gateway devices, mobile phones, public-address systems, car audio systems or music players or a combination thereof. The audio gateway is adapted to receive a multitude of audio signals such as from an entertainment device like a TV or a music player, a telephone apparatus like a mobile telephone or a computer, a PC. The audio gateway is further adapted to select and/or combine an appropriate one of the received audio signals (or combination of signals) for transmission to the at least one hearing device. The remote control is adapted to control functionality and operation of the at least one hearing devices. The function of the remote control may be implemented in a SmartPhone or other electronic device, the SmartPhone/electronic device possibly running an application that controls functionality of the at least one hearing device.

In general, a hearing device includes i) an input unit such as a microphone for receiving an acoustic signal from a user's surroundings and providing a corresponding input audio signal, and/or ii) a receiving unit for electronically receiving an input audio signal. The hearing device further includes a signal processing unit for processing the input audio signal and an output unit for providing an audible signal to the user in dependence on the processed audio signal.

The input unit may include multiple input microphones, e.g. for providing direction-dependent audio signal processing. Such directional microphone system is adapted to enhance a target acoustic source among a multitude of acoustic sources in the user's environment. In one aspect, the directional system is adapted to detect (such as adaptively detect) from which direction a particular part of the microphone signal originates. This may be achieved by using conventionally known methods. The signal processing unit may include amplifier that is adapted to apply a frequency dependent gain to the input audio signal. The signal processing unit may further be adapted to provide other relevant functionality such as compression, noise reduction, etc. The output unit may include an output transducer such as a loudspeaker/receiver for providing an air-borne acoustic signal transcutaneously or percutaneously to the skull bone or a vibrator for providing a structure-borne or liquid-borne acoustic signal. In some hearing devices, the output unit may include one or more output electrodes for providing the electric signals such as in a Cochlear Implant.

A Cochlear Implant typically includes i) an external part for picking up and processing sound from the environment, and for determining sequences of pulses for stimulation of the electrodes in dependence on the current input sound, ii) a (typically wireless, e.g. inductive) communication link for simultaneously transmitting information about the stimulation sequences and for transferring energy to iii) an implanted part allowing the stimulation to be generated and applied to a number of electrodes, which are implantable in different locations of the cochlea allowing a stimulation of different frequencies of the audible range. Such systems are e.g. described in U.S. Pat. No. 4,207,441 and in U.S. Pat. No. 4,532,930.

In an aspect, the hearing device comprises multi-electrode array e.g. in the form of a carrier comprising a multitude of electrodes adapted for being located in the cochlea in proximity of an auditory nerve of the user. The carrier is preferably made of a flexible material to allow proper positioning of the electrodes in the cochlea such that the electrodes may be inserted in cochlea of a recipient. Preferably, the individual electrodes are spatially distributed along the length of the carrier to provide a corresponding spatial distribution along the cochlear nerve in cochlea when the carrier is inserted in cochlea.

Functional Near-Infrared Spectroscopy (fNIR or (NIRS) is the use of NIRS (near-infrared spectroscopy) for the purpose of functional neuroimaging. Using fNIR, brain activity is measured through hemodynamic responses associated with neuron behavior.

There are two different useful responses:
changes in oxygenated hemoglobin (HbO), which measure an expected increase of concentration due to the augmented blood supply required by the neuronal activation, and
deoxygenated hemoglobin (HbR), which is predicted to decrease due to increased oxygen consumption occurring at the cortical site of activation.

FNIR measures hemodynamic changes at the cortex similar to the aforementioned fMRI. In contrast to fMRI, fNIRS measures in quiet (no canning sound), has a higher temporal resolution and can be used to measure brain activity in ecological positions, i.e. sitting at a PC or walking around.

Another advantage of the fNIRS is that it provides a real-time feedback, and that signal processing for fNIRS is less computational compared to fMRI.

EEG and fNIRS complement each other well. EEG has a low spatial but high temporal resolution, whereas fNIRS has a low temporal but high spatial resolution.

Also, fNIRS is not sensitive to CI electrical artifacts (or electrical artifacts generated by e.g. eye movements).

FNIRS works poorly for people with very dark hair (e.g. Asian people), as the NIR penetrates the dark hair embedded in the skin worse.

Also for this reason, according to an aspect of the disclosure, for recording brain responses continuously in real life for CI patients, fNIRS or a combination of fNIRS and EEG is suggested.

It is however unclear how deeply into the brain NIRS measures in practice.

To overcome problems associated with fMRI discussed above, feasibility of functional near-infrared spectroscopy (fNIRS) to image brain activity in response to speech is studied. This approach is proven to be safe and appropriate for use in assessing language development in children.

Consistent with the fMRI literature, fNIRS also demonstrated that the more distorted the speech was, the less region-specific brain activation was observed.

It is thus proposed, according to an aspect of the disclosure, to provide for a wearable functional Near Infrared Red Spectroscopy (fNIRS) for recording cortical responses with a CI system or HA system.

In particular, according to aspects of the disclosure a wearable fNIRS system is provided, where transmitting NIR LEDs are embedded on the back of a CI implant device. NIR sensors located at the back of the implant can detect reflected NIR light and the implant processor (e.g. a digital signal processor (DSP)) can process the signals and provide cortical responses to acoustic input.

This may be used for adapting the signal processing in a hearing device, or simply as part of a diagnostic procedure during fitting. It may also be used for other diagnostic purposes like detection of changes in hemodynamics due to e.g. a diabetes condition, stroke etc.

The above structure may also be applied as part of a behind the ear (BTE) hearing aid design (LEDs and NIR sensors on back of HA shell or in the ear canal).

Such an fNIRS setup may be combined with an earEEG (in the ear EEG electrodes) or implantEEG (using intra-cochlear and extra-cochlear CI implant electrodes for EEG recording) to obtain high spatial and temporal resolution.

The fNIRS system may be active at times of high stimulation activity in a CI system, and the EEG recording system may be applied when limited stimulation is needed.

It has also been shown that fNIRS is measurement sensitive to detect a user's intention (e.g. a subjective preference for a beverage). I.e. it can be also utilized for a BCI through fNIRS-based neuro-feedback.

With the above mentioned principles, one is also able to monitor changes in brain activity deepening on "listening effort". That is, one could maybe detect an "significant" increase in effort in certain listening situation or with a certain HA setting.

Research with preverbal infants has demonstrated the utility of NIRS for studying early speech perception, and the emergence of language laterality.

That is, one can use fNIRS to study speech processing and development of speech processing in the early time after CI activation.

Investigations showed that NIRS may allow for the accurate assessment of the ability of a CI to successfully stimulate the auditory cortex. This supports the notion that NIRS neuroimaging could help guide post-implant programming and therapy in the service of improving deaf children's speech and language outcomes.

The fNIRS recording may also serve as an input for artefact reduction in EEG recordings.

By placing the NIR LEDs directly on the skull under the skin, the loss due to transmitting through the skin is avoided, and a lower power to drive the LEDs is anticipated.

Also the problem of using fNIRS on dark haired people can be avoided.

The physical distance between the LED and the photodiode determine the depth of penetration of the NIR signal. In particular, the larger the selected distance is, the larger the lightened volume is.

Figure 4:
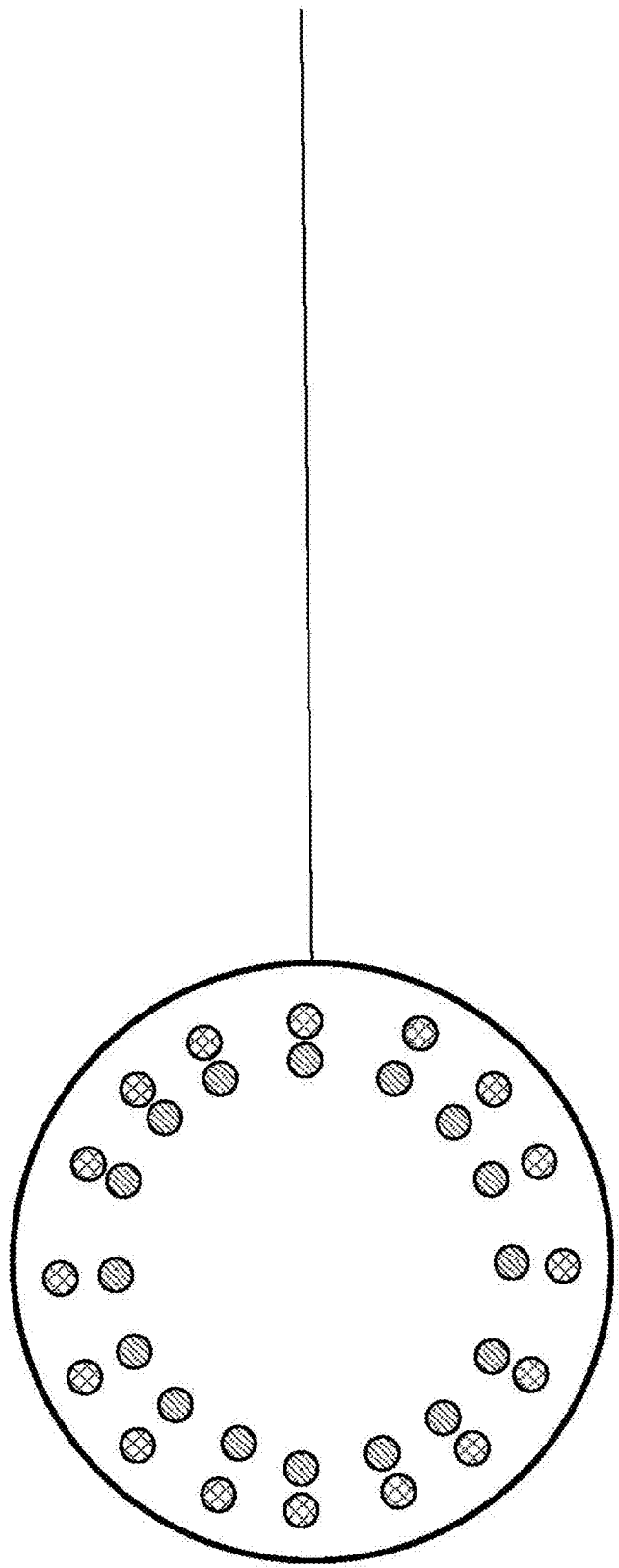
FIG. 4 illustrates an arrangement of near-infrared elements according to an embodiment of the disclosure.

FIG. 4 illustrates an arrangement of near-infrared elements according to an embodiment of the disclosure.

Figure 5:
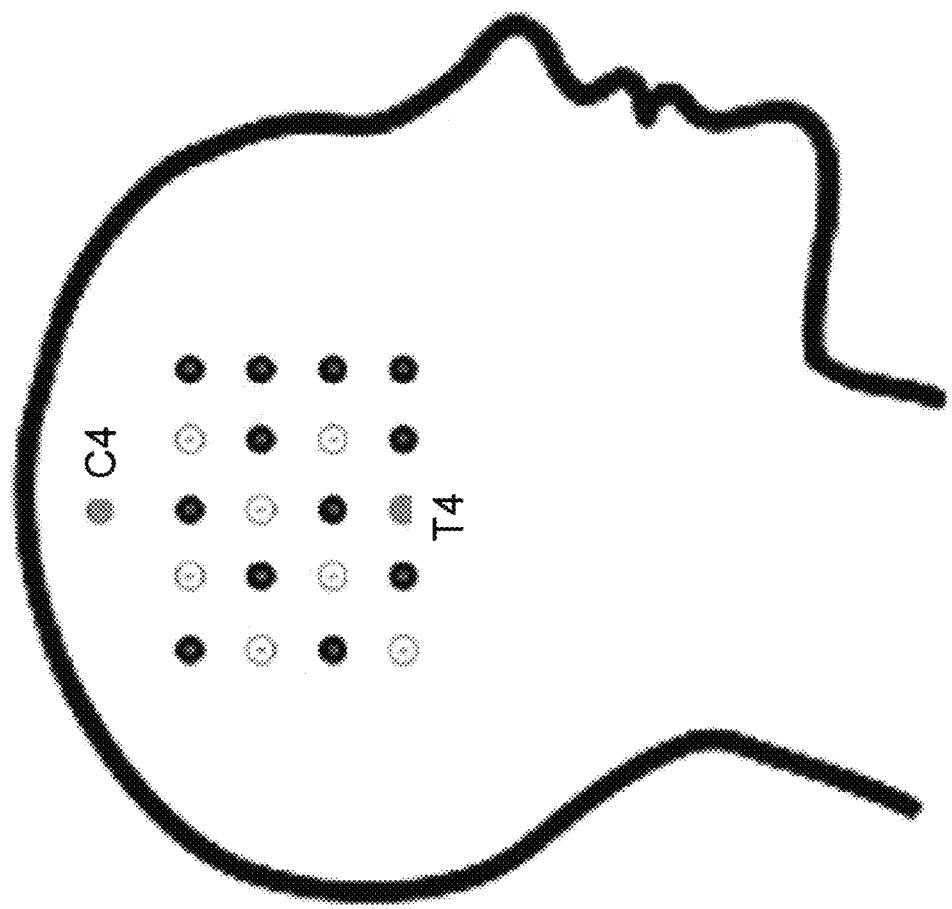
FIG. 5 illustrates an arrangement of near-infrared elements in relation to a head of a user according to an embodiment of the disclosure.

FIG. 5 illustrates an arrangement of near-infrared elements in relation to a head of a user according to an embodiment of the disclosure.

Each illumination channel may consists of two co-located LEDs with emission wavelengths of 760 nm and 850 nm and a miniature collimating lens. Light collection may be achieved with optical fiber bundles coupled to silicon photodetectors.

Now referring to FIG. 1, which illustrates a cochlear implant hearing aid system according to an embodiment of the disclosure.

The cochlear implant hearing aid system 10 comprises an external part 11 and an implant part 12. The cochlear implant hearing aid system 10 further comprises a near-infrared transmitter 13 configured to transmit a near-infrared wave, and a near-infrared receiver 14 configured to receive said near-infrared wave.

The near-infrared transmitter 13 may be provided on either of the external part 11 and the implant part 12 as set out below in more detail.

The near-infrared receiver 14 may be provided on either of the external part 11 and the implant part 12 as well, as set out below in more detail.

Figure 2:
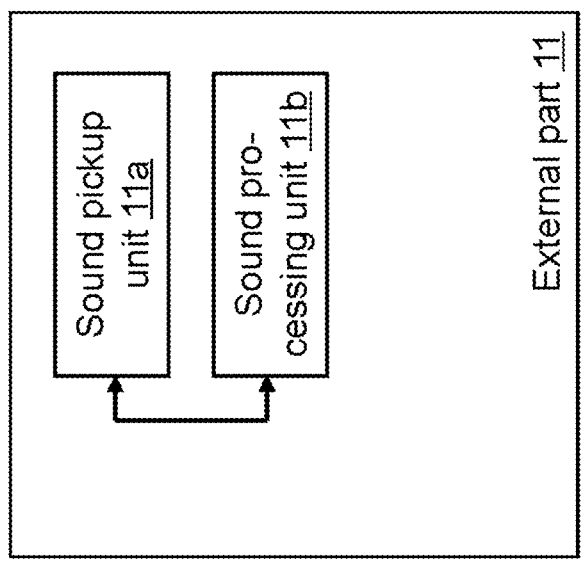
FIG. 2 illustrates details of a cochlear implant hearing aid system according to an embodiment of the disclosure.

Now referring to FIG. 2, which illustrates details of a cochlear implant hearing aid system according to an embodiment of the disclosure. In particular, FIG. 2 illustrates details of the external part 11.

The external part 11 includes a sound pickup unit 11a configured to pick up sound from the environment and a sound processing unit 11b configured to process said sound.

Figure 3:
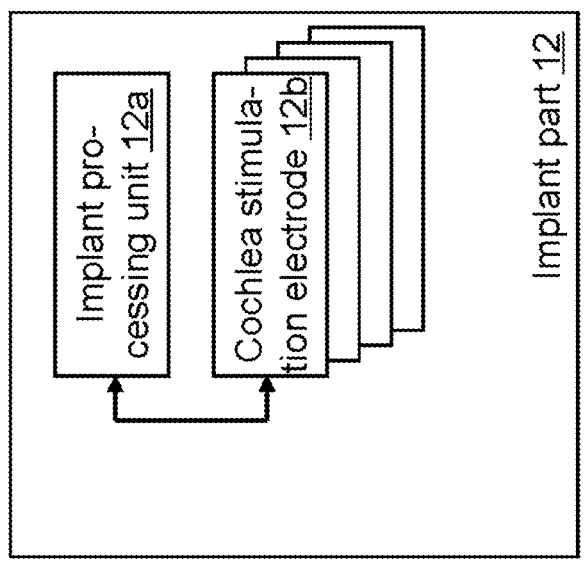
FIG. 3 illustrates details of a cochlear implant hearing aid system according to an embodiment of the disclosure.

Now referring to FIG. 3, which illustrates details of a cochlear implant hearing aid system according to an embodiment of the disclosure. In particular, FIG. 3 illustrates details of the implant part 12.

The implant part 12 includes an implant processing unit 12a and a plurality of cochlea stimulation electrodes 12b for stimulation of a cochlea of a user.

Figure 6:
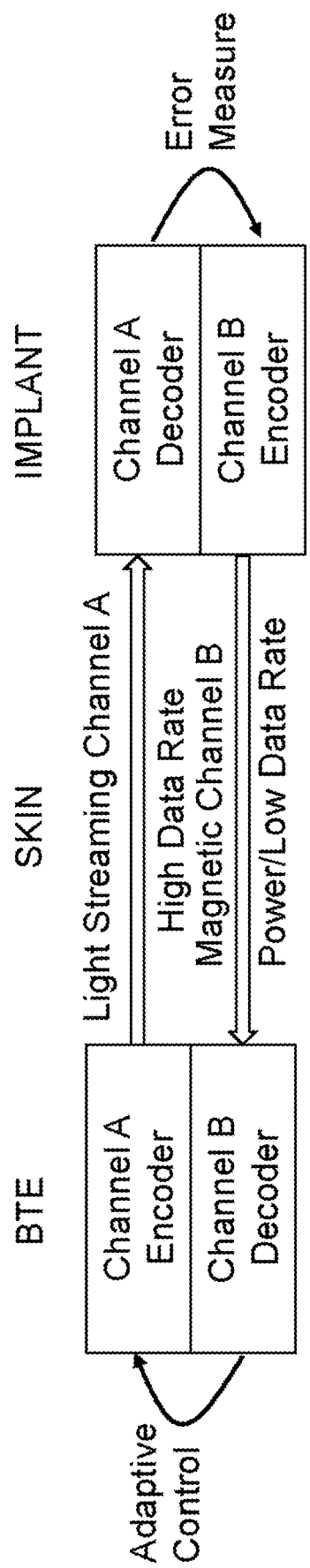
FIG. 6 illustrates a schematic overview on power and data transmission according to an embodiment of the disclosure.

Now referring to FIG. 6, which illustrates a schematic overview on power and data transmission according to an embodiment of the disclosure.

According to embodiments of the disclosure, magnetic induction technology for power transfer/reverse data transfer is combined with near infra-red (NIR) light transmission for forward data transfer. The combination of these technologies allows a better solution than any of these could provide on their own with the magnetic link used to adapt and adjust the light link data transfer as well as its own power transfer. The magnetic link also provides any other required data to be returned from e.g. the implant of a CI to the BTE.

Accordingly, FIG. 6 illustrates a hybrid light/magnetic data and power block diagram for providing high data rate channel to the implant using light, while using a magnetic link to send power to the implant and receive an independent and therefore non-interfering and asynchronous low rate return data from the implant to (1) provide feedback to optimize power transfer, (2) provide feedback to optimize forward data transfer, (3) and provide any other raw return data (e.g. measurement data) from the implant simultaneously and forward data transfers are happening.

Generally, data transfer requirements for forward and reverse data in a CI may be different. Specifically, forward rates must be high (>320 kbps) to sustain the data into the head while reverse data is generally lower in bandwidth and intermittent in nature. These two streams should be full-duplex (i.e. they should allow simultaneous non-interfering forward and reverse transfer). This is an important requirement for adding advanced CI controls (e.g. brainwave feedback) or providing feedback to maintain the data and power links at optimal levels for changing environments. As absolute timing for both streams is becoming more important, the only way to decouple these enough to provide asynchronous and accurate transfers in both directions these must be done in two separate domains. By separating these domains and making them more independent, the different requirements can be decoupled. By using separate methods of transmission, any interference between them can be avoided.

Figure 8:
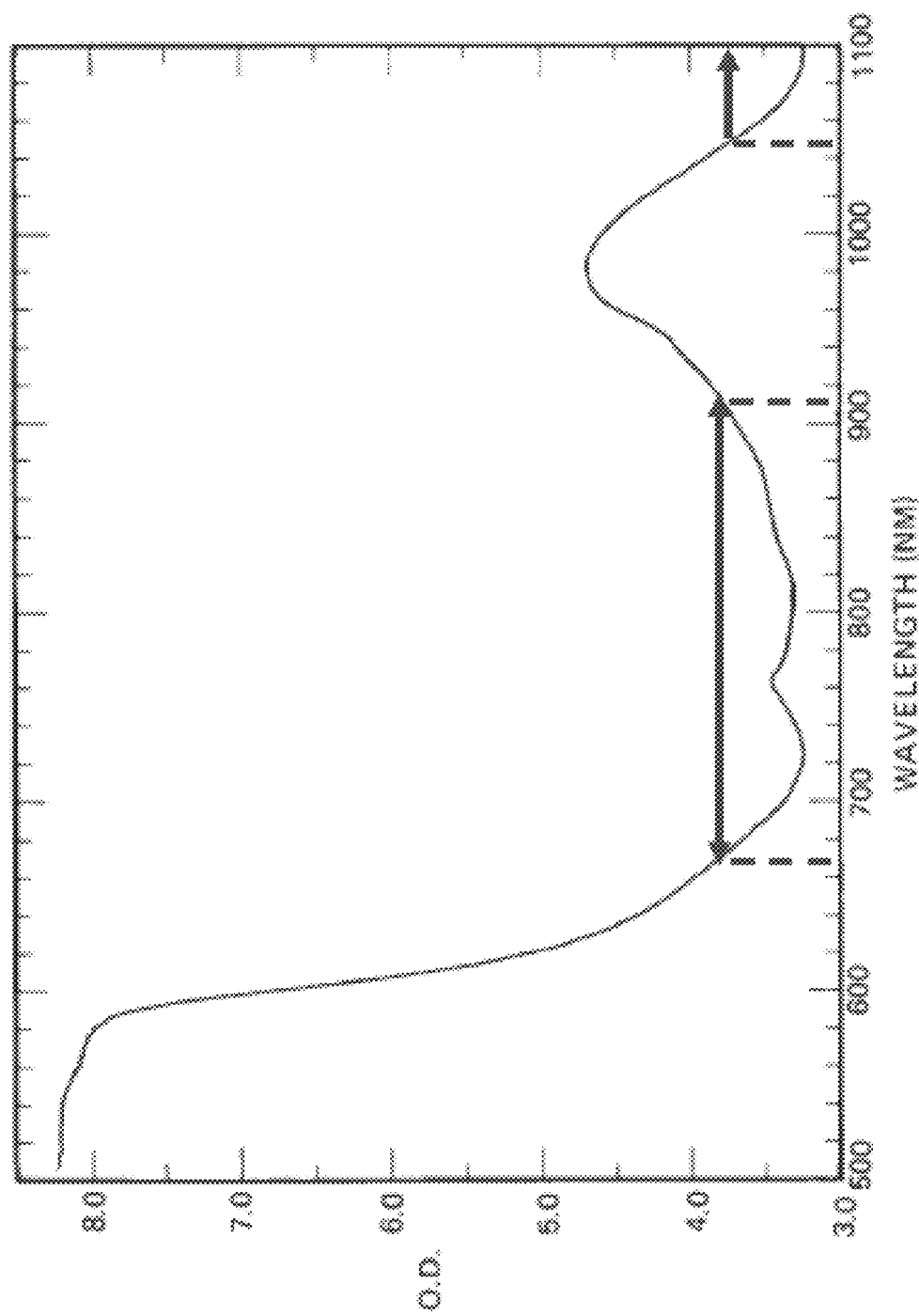
FIG. 8 is a diagram illustrating relative light absorption of a human hand for different wavelengths according to an embodiment of the disclosure.

FIG. 8, is a diagram illustrating relative light absorption of a human hand for different wavelengths according to an embodiment of the disclosure, where measurement are made with a photodiode.

Other available experiments agree that 810 nm is a preferable choice for maximal penetration of most tissues.

With IR systems the key specifications of (1) robustness or reliability, (2) energy/bit, and (3) data rate can all be calculated analytically and compared for different modulation schemes providing that they are applied to the same channel.

The channel properties are fixed after determining the optimal light wavelength and by the thickness of a given skin flap so theoretical calculations of these can be done.

With IR systems only modulations supporting binary transitions were considered. Standard RZI (return to zero inverted), 4-PPM (4 position pulse modulation), "Hirt, Hassner, Heise" (HHH) and the recent EPM (edge position modulation) schemes were compared in the table below:

| Modulation scheme | 1/4-RZI | 4-PPM | HHH(1, 13) | EPM(5, 12, 1/3, 1) |
|---|---|---|---|---|
| Bandwidth efficiency | 0.25 | 0.5 | 0.667 | 1 |
| Bit rate with $T_{pulse}$ = 125 ns | 2 Mbit/s | 4 Mbit/s | 5.33 Mbit/s | 8 Mbit/s |
| Power efficiency | 2 | 2 | 2.584 | 3.448 |
| Quantization error probability under worst case conditions | 5.50E−80 | 6.04E−110 | 4.46E−71 | 1.96E−89 |
| Sample clock frequency | 2 MHz | 8 MHz | 8 MHz | 24 MHz |
| Maximum absolute sample clock phase deviation | ±53.33 ns | ±56.07 ns | ±53.59 ns | ±12.67 ns |
| Maximum relative sample clock phase deviation | ±10.7% | ±45% | ±43% | ±30% |
| Maximum sequence length without '0' to '1' transitions | ∞ | 6 | 13 | 12 |

Although above requirements for a higher data rate towards the CI and a lower data rate from the CI are discussed, in specific use cases, the data rate requirements may be vice versa. Accordingly, according to some embodiments of the disclosure, the discussed elements may be arranged such that opposite data rate requirements were fulfilled.

Figure 7:
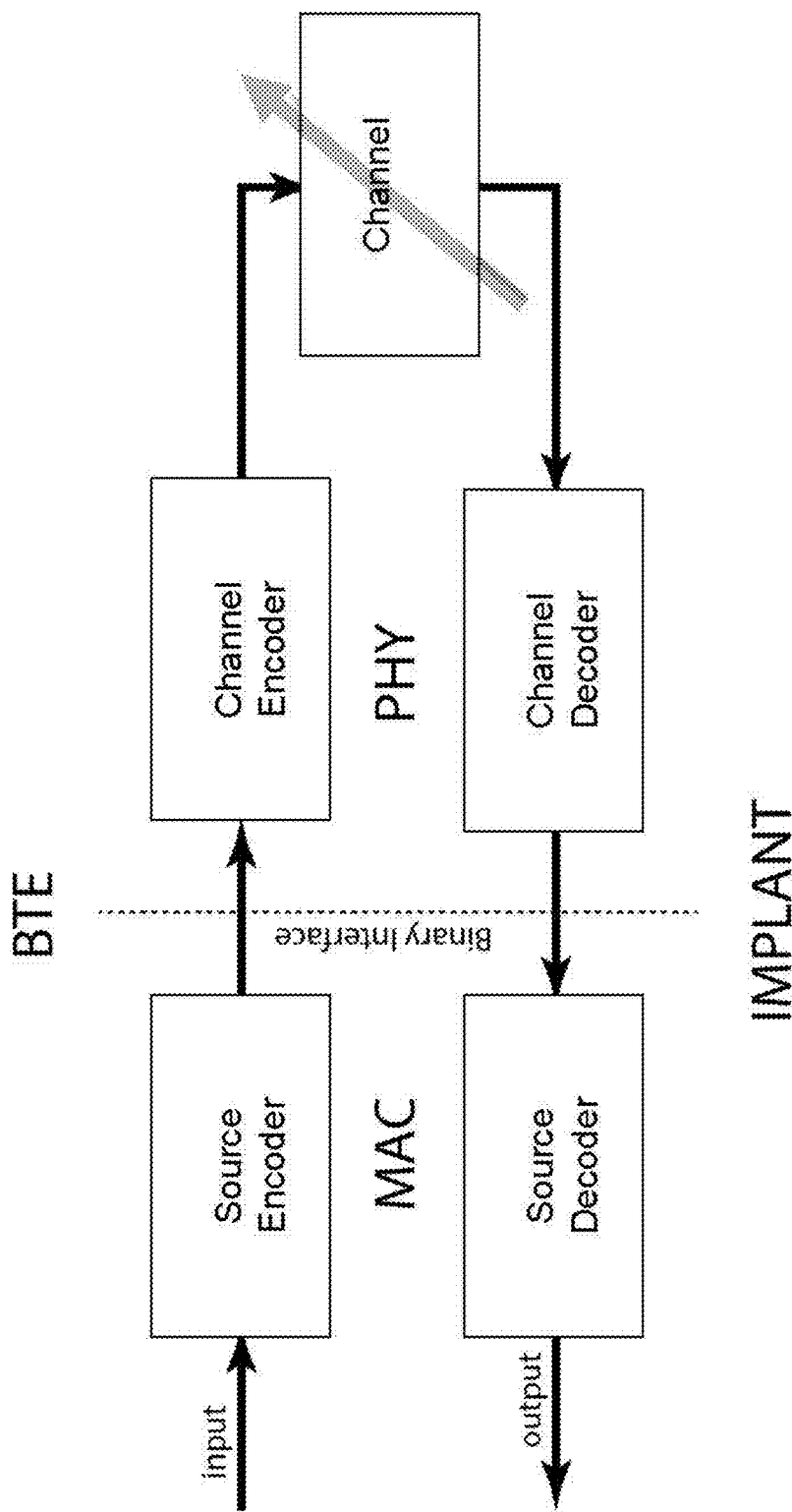
FIG. 7 illustrates a schematic overview on data transmission according to an embodiment of the disclosure.

Now referring to FIG. 7, which illustrates a schematic overview on data transmission according to an embodiment of the disclosure.

In general sending can be broken down into four engineered blocks for encoding and receiving, and one block that varies with the environment. In the present CI case, this variation is generally (dependent on) the skin thickness.

Accordingly, FIG. 7 depicts a communication architecture block diagram, which shows the digital and physical encoding and decoding blocks explicitly. The channel is affected by the environment notably skin thickness. Feedback allows adjusting for changing environmental channels.

In the following, forward data transmission using the near infrared technology is considered.

The transmission of data across the skin (forward data transmission) for the CI application requires high data rates and increasingly must be robust against interference with asynchronous timing.

Current technologies for brain imaging (fNIR) have adopted using IR wavelengths. Generally, these wavelengths are 810 or 840 nm in the 'near' infra-red spectrum (700-900 nm). The advent of this technology has increased the availability of LEDs and photodiodes that produce and receive these wavelengths for medical applications. Tissues such as the scalp are transparent to these wavelengths.

All IR-based modulation techniques demonstrated a sufficient bit-rate to meet the 320 kbps required (based on a channel permitting pulse widths of 125 ns which is an IrDA standard pulse width).

The shown EPM variant provided the best bandwidth efficiency and transmit power efficiency, however, required a higher frequency, more accurate sample clock, and added decoding complexity (state machine with 1 internal state vs. straight decode).

Further, because EPM is based on edge detection, elongated pulses do not create errors as they do for 4-PPM.

A hardware circuit was built using standard components to assess the physical channel behavior for IR communication viability.

With respect to the thus tested forward data transmission system, the physical layer of the system was tested for speed by way of an mask test (½ eye diagram) in the presence of 13 mm of skin (human hand) and the current ceramic implant ceramic ZTI covering material. The system was unshielded and was found to be subject to EM (RF interference). This could be controlled with better circuit shielding. The used photodiode may not have been the most effective and did not have any daylight blocking filters, an alternate (BPV22NF) was also tried and did perform a bit better but could not provide a shielded case so was less immune to interference.

With respect to the thus tested reverse data transmission system, the reverse data transmission and power optimization feedback uses a carrier (in our case either 6.78 MHz or 4 MHz) sent from the BTE to provide continuous power. For reverse data transfer this carrier is load-modulated by switching a capacitor (or other passive element) to produce a small change in the impedance seen at the BTE, which is then decoded. This is commonly used in NFC communications and is well documented.

As mentioned above, the return data is used to adapt and optimize both the magnetic link and provide error rate information to adapt and optimize the light link. Because the transmit energy required may change depending on the skin thickness, an automatic adaptive algorithm that receives return data and sets the IR LED transmitted forward voltage is possible. A variable voltage block would provide the control.

In sum, the aspects discussed above are also combinable as follows.

Namely, according to a further aspect of the present disclosure, the LED(s) (i.e. near-infrared transmitter) is/are placed outside the head of the user and the detector (i.e. near-infrared receiver) is placed below the skin of the user, while the power supply and the reverse data transmission are embodied by the (electro)magnetic link. According to this aspect, the detector i.e. near-infrared receiver) may be configured to both receive scattered wavelength signals from within the head of the user and to receive the directly transmitted wavelength signal.

According to a further aspect of the present disclosure, the LED(s) (i.e. near-infrared transmitter) is/are placed below the skin and the detector (i.e. near-infrared receiver) is placed outside the head. Here, at least the power supply may be embodied by the (electro)magnetic link.

Figure 9A:
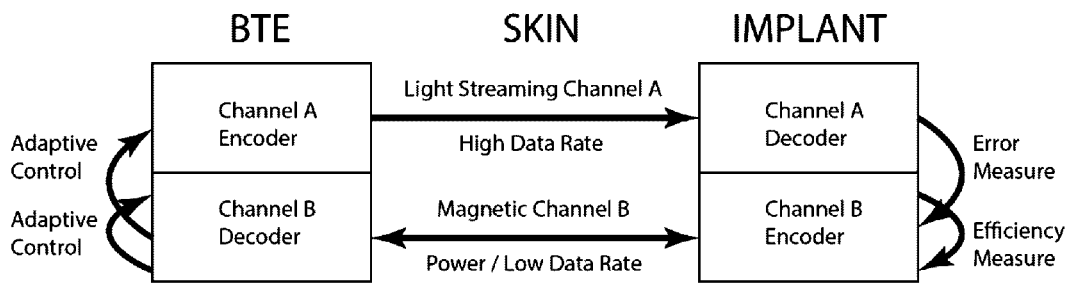
FIG. 9A to 9C illustrate a schematic overview on power and data transmission according to an embodiment of the disclosure.
Figure 9B:
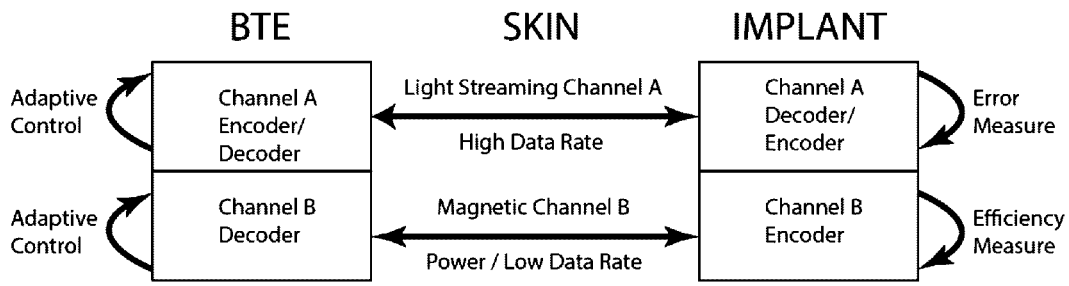
Figure 9C:
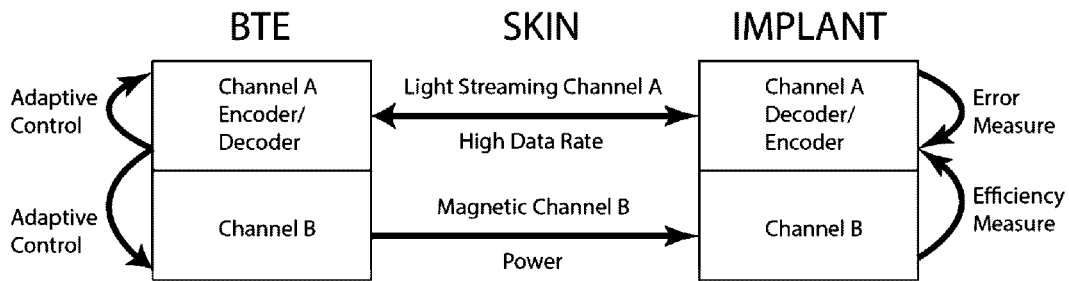

FIG. 9A-9C illustrate three different examples on a schematic overview on power and data transmission according to an embodiment of the disclosure.

FIG. 9A illustrates an example where the data is returned on a low rate magnetic channel but sent on a high rate light channel.

FIG. 9B illustrates an example where the data is return on a high rate light channel, sent on a high rate light channel and only power is delivered on the Magnetic channel.

FIG. 9C illustrates an example where the data is sent and received on a high rate light channel which controls it's own error rate. Power and return data is sent on the magnetic channel. If the return data on the EM channel carries link efficiency and/or power requirement information, it allows the two systems to be independent.

As used, the singular forms "a," "an," and "the" are intended to include the plural forms as well (i.e. to have the meaning "at least one"), unless expressly stated otherwise. It will be further understood that the terms "includes," "comprises," "including," and/or "comprising," when used in this specification, specify the presence of stated features, integers, steps, operations, elements, and/or components, but do not preclude the presence or addition of one or more other features, integers, steps, operations, elements, components, and/or groups thereof. It will also be understood that when an element is referred to as being "connected" or "coupled" to another element, it can be directly connected or coupled to the other element but an intervening elements may also be present, unless expressly stated otherwise. Furthermore, "connected" or "coupled" as used herein may include wirelessly connected or coupled. As used herein, the term "and/or" includes any and all combinations of one or more of the associated listed items. The steps of any disclosed method is not limited to the exact order stated herein, unless expressly stated otherwise.

It should be appreciated that reference throughout this specification to "one embodiment" or "an embodiment" or "an aspect" or features included as "may" means that a particular feature, structure or characteristic described in connection with the embodiment is included in at least one embodiment of the disclosure. Furthermore, the particular features, structures or characteristics may be combined as suitable in one or more embodiments of the disclosure. The previous description is provided to enable any person skilled in the art to practice the various aspects described herein. Various modifications to these aspects will be readily apparent to those skilled in the art, and the generic principles defined herein may be applied to other aspects.

The claims are not intended to be limited to the aspects shown herein, but is to be accorded the full scope consistent with the language of the claims, wherein reference to an element in the singular is not intended to mean "one and only one" unless specifically so stated, but rather "one or more." Unless specifically stated otherwise, the term "some" refers to one or more.

Accordingly, the scope should be judged in terms of the claims that follow.

The invention claimed is:

1. A cochlear implant hearing aid system, comprising
an external part including a sound pickup unit configured to pick up sound from the environment and a sound processing unit configured to process said sound,
an implant part including an implant processing unit and a plurality of cochlea stimulation electrodes for stimulation of a cochlea of a user, wherein the implant processing unit is disposed within a component configured to be arranged between a skin and a skull of the user, the component including electromagnetic circuitry configured to establish a power and/or data communication link with the external part, the cochlea stimulation electrodes being disposed on a carrier extending out of the component,
a near-infrared transmitter configured to transmit near-infrared waves of a wavelength within a range of 700-900 nm, wherein said near-infrared transmitter is an internal near-infrared transmitter provided on said implant part and configured to transmit said near-infrared waves outside of the cochlear implant hearing aid system towards a cortex of said user, and
a near-infrared sensor configured to detect near-infrared waves of a wavelength within the range of 700-900 nm, wherein said near-infrared sensor is an internal near-infrared sensor provided on the component of said implant part and configured to detect said near-infrared waves scattered by said cortex of said user from outside of the cochlear implant hearing aid system,
wherein said near-infrared transmitter and said near-infrared sensor are embedded on a back side of the component of said implant part, and the back side of the component of said implant part is configured to be directed towards the skull of said user, and
wherein said implant processing unit is a digital signal processor configured to process said detected near-infrared waves scattered by said cortex according to Near Infrared Spectroscopy (NIRS) or functional NIRS (fNIRS) image processing to provide cortical responses to sounds picked up by the sound pickup unit.

2. The cochlear implant hearing aid system according to claim 1, wherein
said implant processing unit is programmed with computer-executable instructions to apply said NIRS or fNIRS image processing to extrapolate, from said detected near-infrared waves scattered by said cortex, a hemodynamic response associated with neuron behavior of said brain of said user, and to output a determined brain activity of a brain of said user based on said hemodynamic response.

3. The cochlear implant hearing aid system according to claim 2, wherein
a result of said implant processing unit is used for adapting a signal processing of said cochlear implant hearing aid system, for adapting a processing of said sound by said sound processing unit, for fitting said cochlear implant hearing aid system to said user, for health condition monitoring of said user, and/or for an output of a brain-computer-interface.

4. The cochlear implant hearing aid system according to claim 1, further comprising
an electromagnetic power transmission unit provided on said external part and configured to transmit electromagnetic power in a non-contact manner, and
an electromagnetic power receiving unit provided as part of the electromagnetic circuitry on the front side of the component, the electromagnetic power receiving unit being configured to receive said electromagnetic power in a non-contact manner, wherein
said implant part is configured to utilize said electromagnetic power as a power supply.

5. The cochlear implant hearing aid system according to claim 4, further comprising
an electromagnetic data transmission unit provided as part of the electromagnetic circuitry on the front side of the component, the electromagnetic data transmission unit being configured to transmit data in a non-contact manner utilizing an electromagnetic field generated by said electromagnetic power transmission unit for transmission of said electromagnetic power, and
an electromagnetic data receiving unit provided on said external part and configured to receive said data in a non-contact manner.

6. The cochlear implant hearing aid system according to claim 5, further comprising
a power adjustment unit provided on said external part and configured to adjust, based on said data, said electromagnetic power transmitted by said electromagnetic power transmission unit.

7. The cochlear implant hearing aid system according to claim 1, wherein said near-infrared transmitter and said near-infrared sensor are respectively oriented on the back side of the component of said implant part to:
configure said near-infrared transmitter so that a primary direction of near-infrared transmission is directed at said cortex, and
configure said near-infrared sensor so that a primary direction of near-infrared detection is directed at said cortex.

8. The cochlear implant hearing aid system according to claim 1, wherein the near-infrared transmitter is a near-infrared light emitting diode embedded on the back side of the component so as to emit near-infrared light directly from the back side of the component.

9. The cochlear implant hearing aid system according to claim 1, wherein the near-infrared light sensor is electrically connected to said implant processing unit whereby the near-infrared light sensor sends an electrical signal representing a result of detection to the implant processing unit for processing.

10. The cochlear implant hearing aid system according to claim 1, wherein a plurality of near-infrared transmitters and near-infrared sensors are embedded on the back side of the component and arranged in a substantially co-planar pattern where each near-infrared transmitter is disposed next to a corresponding one of the near-infrared sensors.

11. The cochlear implant hearing aid system according to claim 1, wherein the electromagnetic circuitry is disposed on a front side of the component.

12. A cochlear implant hearing aid system, comprising
an external part including a sound pickup unit configured to pick up sound from the environment and a sound processing unit configured to process said sound,
an implant part including an implant processing unit and a plurality of cochlea stimulation electrodes for stimulation of a cochlea of a user, wherein the implant processing unit is disposed within a component configured to be arranged between a skin and a skull of the user, the component including electromagnetic circuitry configured to establish a power and/or data communication link with the external part, the cochlea stimulation electrodes being disposed on a carrier extending out of the component,
a near-infrared transmitter configured to transmit near-infrared waves of a wavelength within a range of 700-900 nm, wherein said near-infrared transmitter is configured to transmit said near-infrared wave through tissue towards a cortex of said user, and
a near-infrared sensor configured to detect near-infrared waves of a wavelength within the range of 700-900 nm, wherein said near-infrared sensor is configured to detect said near-infrared waves scattered by the near-infrared wave interacting with said cortex of said user,
wherein the external part comprises the near-infrared transmitter and the implant part comprises the near-infrared sensor, or wherein the implant part comprises the near-infrared transmitter and the external part comprises the near-infrared sensor, and
wherein said implant processing unit is a digital signal processor configured to process said detected near-infrared waves scattered by said cortex according to Near Infrared Spectroscopy (NIRS) or functional NIRS (fNIRS) image processing to provide cortical responses to sounds picked up by the sound pickup unit.

13. A cochlear implant hearing aid system, comprising
an external part including a sound pickup unit configured to pick up sound from the environment and a sound processing unit configured to process said sound,
an implant part including an implant processing unit and a plurality of cochlea stimulation electrodes for stimulation of a cochlea of a user, wherein the implant processing unit is disposed within a component configured to be arranged between a skin and a skull of the user, the component including electromagnetic circuitry configured to establish a power and/or data communication link with the external part, the cochlea stimulation electrodes being disposed on a carrier extending out of the component,
a near-infrared transmitter configured to transmit near-infrared waves having a wavelength of 700-900 nm through tissue to a near-infrared sensor;
wherein said near-infrared transmitter is an internal near-infrared transmitter provided on said implant part and configured to transmit said near-infrared wave towards a cortex of said user,
wherein said near-infrared sensor is an internal near-infrared sensor provided on the component of said implant part and configured to detect said near-infrared waves scattered by said cortex of said user, and
wherein said implant processing unit is a digital signal processor configured to process said detected near-infrared waves scattered by said cortex according to Near Infrared Spectroscopy (NIRS) or functional NIRS (fNIRS) image processing to provide cortical responses to sounds picked up by the sound pickup unit.

* * * * *